United States Patent [19]

Umezawa et al.

[11] 3,959,257

[45] May 25, 1976

[54] PRODUCTION OF COFORMYCIN AND INTERMEDIATES THEREFOR

[75] Inventors: Hamao Umezawa; Kenji Maeda, both of Tokyo; Shinichi Kondo, Yokohama, all of Japan

[73] Assignee: Zaidan Hojin Biseibutsu Kagaku Kenkyu Kai, Japan

[22] Filed: Oct. 24, 1974

[21] Appl. No.: 518,030

[30] Foreign Application Priority Data

Nov. 14, 1973  Japan.............................. 48-127174

[52] U.S. Cl..................... 260/211.5 R; 204/158 R; 424/180
[51] Int. Cl.².......................................... C07H 19/18
[58] Field of Search........... 260/211.5, 309, 211.5 R

[56] References Cited
UNITED STATES PATENTS 3,535,207  10/1970  Shiro et al.................... 260/211.5 R

OTHER PUBLICATIONS

Hudson, "Advances In Carbohydrate Chemistry", Vol. 8, 1953, Academic Press Inc. New York, N.Y., pp. 112–115.
Sawa et al. "Jour. Antibotics, Ser. A." Vol. 20, No. 4, pp. 227–231, July, 1967.
Ohno et al. "Jour. Amer. Chem. Soc." Vol. 96, No. 13, pp. 4326–4327, June, 1974.
Nakamura et al. "Jour. Amer. Chem. Soc." Vol. 96, No. 13, pp. 4327–4328, June, 1974.

*Primary Examiner*—Johnnie R. Brown
*Attorney, Agent, or Firm*—Herbert W. Taylor, Jr.

[57] ABSTRACT

This invention relates to a process for the preparation of coformycin, 3-($\beta$-D-ribofuranosyl)-6,7,8-trihydroimidazo[4,5-d][1,3]diazepin-8(R)-ol, through a synthetic route from a new derivative of 9-$\beta$-D-ribofuranosyl-purine and other synthetic intermediates involved in the process and their preparation.

4 Claims, No Drawings

PRODUCTION OF COFORMYCIN AND INTERMEDIATES THEREFOR

BACKGROUND OF THE INVENTION

1. Field of the Invention

This invention relates to chemical compounds of the type called nucleosides as produced by chemical synthesis and includes various processes and intermediates.

2. Description of the Prior Art

Coformycin is a substance found and isolated from culture broth of Nocardia interforma and Streptomyces kaniharaensis SF-577 which are formycin-producing strains and has interesting biological and physiological activities. Namely, coformycin alone has no antibiotic activity as such, but exhibits a strong synergistic activity with formycin in inhibiting the growth of bacteria. [see Scientific Reports of Meiji Seika Kaisha, 9, 17 and 22 (1967)] and remarkably inhibits the enzymatic deamination reaction of formycin and adenosine [see H. Umezawa et al., Journal of Antibiotics, Ser. A. 20, 227 (1967)]. Therefore, coformycin is very important not only in the analysis of the cause of diseases relevant to nucleic metabolism, but also in the chemotherapy of certain diseases.

SUMMARY OF THE INVENTION

We have now found that a new derivative of 9-β-D-ribofuranosylpurine, identified as 9-(2,3,5-tri-O-acyl-β-D-ribofuranosyl)-6-mesyloxymethyl-1,6-dihydropurine, undergoes a ring expansion reaction under a basic condition, giving coformycin.

A primary object of this invention, therefore, is to provide a first process for the synthesis of coformycin from a new derivative of 9-β-D-ribofuranosylpurine which is easily available.

Another object of this invention is to provide new intermediate compounds, namely new derivatives of 9-β-D-ribofuranosylpurine.

A further object of this invention is to provide processes for the preparation of such new derivatives of 9-β-D-ribofuranosylpurine.

According to this invention, therefore, there is provided a process for the preparation of coformycin of the formula (I):

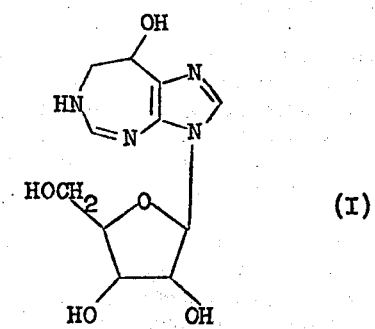

which comprises treating 9-(2,3,5-tri-O-acyl-β-D-ribofuranosyl)-6-mesyloxymethyl-1,6-dihydropurine of the formula (II):

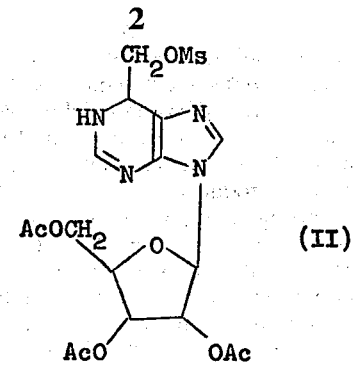

in which Ac represents acetyl and Ms represents mesyl, with a base and hydrolyzing immediately the resulting intermediate product.

In carrying out the process of this invention, the starting compound, 9-(2,3,5-tri-O-acyl-β-D-ribofuranosyl)-6-mesyloxymethyl-1,6-dihydropurine (II), which may be derived from 9-β-D-ribofuranosylpurine as hereinafter described, is treated with a base such as potassium tert.-butoxide, sodium hydride or triethylamine in an inert solvent such as dimethoxyethane, tetrahydrofuran, dioxane, dimethylsulfoxide or dimethylformamide under cooling, preferably at a temperature below 30° C. In a preferred embodiment, the starting compound (II) is dissolved in dimethoxyethane, and to the solution is added potassium tert.-butoxide at a temperature of −10 to −15° C. After the addition of base, the reaction is continued at a temperature of −5 to 5° c., say about 0° C. for 15 to 20 hours. The brownish red precipitate formed during the reaction is separated by decantation, washed with the same solvent used in the reaction and dried. The product is then treated with active charcoal and the product adsorbed on the charcoal is extracted with a solvent such as aqueous acetone or aqueous methanol. The extract is then concentrated to give a pale yellow glassy material which is then subjected to desalting in a known manner, for example, by treating with a strong anion-exchange resin. In a preferred embodiment, the hydrolysis is effected by treating the material with an anionexchange resin, Dowex 1-X2 (OH⁻) (Dowex is a registered trade mark), preferably at a pH value of 8 to 8.5 at room temperature for 10 to 20 hours. Thereafter, the reaction mixture is concentrated to yield coformycin as crude product. The purification of the crude product may be carried out in a conventional manner, for example, by preparative thin-layer chromatography of column chromatography, when necessary.

The identity of the coformycin synthesized as above according to this invention with the natural one was confirmed by spectroscopic data including ir, uv and nmr, optical rotation, mixed melting point, etc.

The successful ring expansion of the starting mesyl derivative (II) into coformycin undoubtedly suggests that the reaction was conducted through an aziridine intermediate of the formula (III):

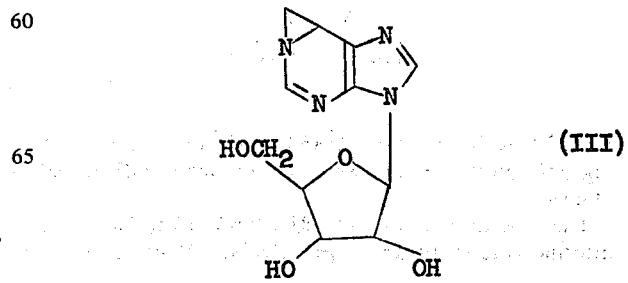

although the said intermediate was not isolated in the process above, but subjected directly to the subsequent hydrolysis, because the isolation thereof was difficult or complicated due to its instability and the presence of potassium salts of methanesulfonic and acetic acids present as by-products.

The starting compound, 9-(2,3,5-tri-O-acyl-β-D-ribofuranosyl)-6-mesyloxymethyl-1,6-dihydropurine, is in itself new and is derived from the known and relatively easily available 9-β-D-ribofuranosylpurine by a process which comprises (1) acylating 9-β-D-ribofuranosylpurine of the formula (IV):

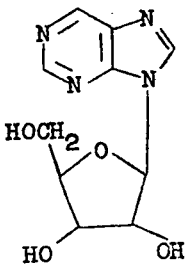

in a manner known per se to give an acylate of the formula (V):

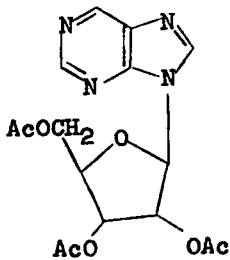

in which Ac represents an acyl group, (2) addition-reacting methanol to the acylate thus obtained under the irradiation of light to form a methanol-adduct of the formula (VI):

in which Ac represents an acyl group and (3) mesylating the methanol-adduct thus obtained with mesyl chloride.

The methanol-adduct of the formula (VI) formed as intermediate in the above process, namely 9-(2,3,5-tri-O-acyl-62 -D-ribofuranosyl)-6-hydroxy-methyl-1,6-dihydropurine, is also a new compound in itself. According to another aspect of this invention, therefore, there are provided, as new compounds, compounds of the formula (VII):

in which Ac represents an acyl group and R represents hydroxyl (VI) or O-mesyl (II). Most typically, Ac represents acetyl group.

This invention also provides a process for the preparation of the new compounds of the formula (VII) which involves the formulae (II) and (VI) comprising the steps (1) and (2) above-mentioned for the compounds of the formula (VI) and comprising the step (3) for the compounds of the formula (II), respectively.

In carrying out the process for the preparation of the new compounds of the formula (VII), the starting compound, 9-β-D-ribofuranosylpurine (IV) which is available through various routes may be acylated by any conventional technique per se to give 2′,3′,5′-tri-O-acyl-9-β-D-ribofuranosylpurine of the formula (V) in a high yield. Thus, the acylation may generally be performed with an acylating agent such as acetyl chloride or acetic anhydride in an inert solvent such as pyridine.

In a preferred embodiment, the acylation is effected with acetic anhydride in pyridine, giving 2′,3′,5′-tri-O-acetyl9-β-D-ribofuranosylpurine in 98% yield. The acylation is effected at a temperature at which both the starting compound and the acylated product are stable, usually at about 0° to 30° C. for about 10 to 50 hours. The triacylated product thus obtained is dissolved in anhydrous methanol and irradiated with light under an inert gas atmosphere, e.g., an argon or nitrogen atmosphere. The photo-reaction should be carried out under such temperature conditions that the cooling of the reaction mixture may be sufficiently effected, preferably at a temperature of about 5° to 10° C. The irradiation source may be any of those capable of supplying a light having wave length of about 254 nm and a low-pressure mercury lamp is preferably used. The completion of the photo-reaction may be determined by the change in UV absorption spectra of the reaction mixture, that is the value of $E_{296}$ nm/$E_{263}$ being 150–160% is taken as the completion of the reaction. Usually, the photoreaction may be completed within 10 hours. The reaction mixture is then concentrated to dryness, giving the methanol-adduct, 9-(2,3,5-tri-O-acyl-β-D-ribofuranosyl)-6-hydroxymethyl-1,6-dihydropurine of the formula (VI), in 96% yield. The hydroxymethyl derivative thus obtained is then dissolved in an inert solvent, e.g., dimethoxyethane, and treated with sodium hydride and then with mesyl chloride under cooling. The reaction is continued for about 10 to 20 hours while the temperature being maintained at about 0° to 5° C. After the completion of the reaction, the reaction mixture is treated with an organic solvent, e.g., chloroform-water in a conventional manner and a pale-yellow oil identified as the mesylated derivative, 9-(2,3,5-tri-O-acyl$\beta$-D-ribofuranosyl)-6-mesyloxymethyl-1,6-dihydropurine of the formula (II) is isolated from the organic layer in a high yield.

This invention is further illustrated with reference to the following Example but is in no way limited thereto.

DESCRIPTION OF THE PREFERRED EMBODIMENTS

Example

1. Preparation of 2',3',5'-tri-O-acetyl9-$\beta$-D-ribofuranosylpurine (V)

9-$\beta$-D-Ribofuranosylpurine (IV) (1.08 g.) was dissolved in acetic anhydride (5 ml.) and pyridine (100 ml.) and acetylated at 5° C. for 2 days. The reaction mixture was then concentrated into a syrup which was then treated with water-chloroform. The chloroform layer thus separated was washed with water, treated with anhydrous sodium sulfate and concentrated to yield (V) as a colorless oil (1.59 g., yield 98%).

Spectral Confirmations

Mass: m/e 379 (M + 1), 378 (M$^+$), 335 (-Ac), 319 (-OAc), 259 (tri-O-acetylribose), 149 (purine + 30).

IR: $\nu$KBr, 1750 (OAc), 1600, 1380, 1200–1240 (OAc), 1100 – 1000 cm$^{-1}$.

UV: $\lambda_{max}^{MeOH}$, 263 ($\epsilon$13,600), 246 nm (shoulder $\epsilon$9,800).

| NMR (CDCl$_3$, 100 MHz): · $\delta$ | 2.08 (3H, S), 2.10 (3H, S), |
|---|---|
| 2.14 (3H, S), | 4.45 (2H, mult., 4',5'-H), |
| | 5.7 (1H, d-d, 3'-H), |
| | 6.0 (1H, d-d, 2'-H), |
| | 6.28 (1H, d, 1'-H) |
| | 8.27 (1H, S), 9.0 (1H, S), |
| 9.18 (1H, S) | |

Specific rotation [$\alpha$]$_D^{26}$ − 10.8° (c= 1.5, MeOH).

2. Preparation of 9-(2,3,5-tri-O-acetyl$\beta$-D-ribofuranosyl)-6-hydroxymethyl-1,6-dihydropurine (VI)

2',3',5'-Tri-O-acetyl-b 9-$\beta$-D-ribofuranosylpurine (V) (90 mg.) obtained in (1) was dissolved in anhydrous methanol (18 ml.) and irradiated with 10 W low-pressure mercury lamp (254 nm) under argon atmosphere with cooling to 5–10° C. The completion of the reaction was determined by the change in UV adsorption of the reaction mixture. The reaction was stopped at a value of E$_{296}$/E$_{263}$ which reached to 150 to 160% (the reaction time: 3–3.5 hours). The reaction mixture was then concentrated to dryness to yield VI as a colorless glassy residue. Yield: 108 mg. (96%).

Elementary Analysis

Calculated for C$_{17}$H$_{22}$N$_4$O$_8$: C, 49.75; H, 5.40; N, 13.65; O, 31.19. Found: C, 49.73; H, 5.44; N, 13.57; O, 3.91.

Spectral Confirmation

UV: $\lambda_{max}^{MeOH}$, 296 ($\epsilon$9,000), 244 nm (5,500)

IR: $\nu$KBr, 1750 (OAc) 1610, 1580 (dihydropurine ring), 1380, 1230 – 1260 (OAc), 1020-1100 cm$^-$.

Mass: 452 (M + 42), 410 (M$^+$), 393 (M — OH). 379 (M — CH$_2$OH), 337 (M — CH$_2$OH — Ac), 259 (tri-O-acetylribose), 223 (base + 30 + 42), 151 (base).

NMR (D$_2$O, 100 MHz): $\delta$2.55 – 2.63 (9H, Ac × 3), $\delta$4.16 (2H, mult., — CH$_2$ —OH), $\delta$5.43 (1H, mult., methine), $\delta$4.85 (2H, 5'—H), $\delta$4.90 (1H, 4'—H), $\delta$5.90 (1H, d—d, 3'—H), $\delta$6.15 (1H, 2'—H), $\delta$6.42 (1H, d, 1'—H), $\delta$7.67 (1H, S), $\delta$8.11 (1H, S)

3. Preparation of 9-(2,3,5-tri-O-acetyl-$\beta$-D-ribofuranosyl)-6-mesyloxymethyl-1,6-dihydropurine (II)

9-(2,3,5-Tri-O-acetyl-$\beta$-D-ribofuranosyl)-6-hydroxymethyl-1,6-dihydropurine (VI) (217 mg.) obtained in (2) was dissolved in purified anhydrous dimethoxyethane (10 ml.) and cooled to −10° to −15° C. To the cooled solution were added sodium hydride (76 mg., 3 moles) and mesyl chloride (180 mg., 3 moles), successively. The reaction was conducted at 0° – 5° C. for 17 hours. The reaction mixture was then treated with water-chloroform and the chloroform layer thus separated was washed with 0.5% aqueous sodium hydrogen carbonate, then with water, dried over anhydrous sodium sulfate and concentrated to yield II as a pale-yellow oil (235 mg., yield: 91%). This substance is unstable and decomposes in chloroform within 2–3 hours.

Spectral Confirmation

IV: $\lambda_{max}^{MeOH}$, 293 ($\epsilon$7,600), 246 nm (shoulder $\epsilon$5,400).

Mass: 488 (M$^+$), 486 (M − 2), 392 (—Ms), 349 (—Ms, —Ac), 333 (—Ms, —OAc), 259 (tri-O-acetylribose), 177 (base + 30 — Ms).

4. Preparation of Coformycin (I)

The mesylated derivative (II) (207 mg.) obtained in (3) was dissolved in dimethoxyethane (20 ml.) and cooled to −10° to −12° C. TO the cooled solution was added potassium tert.-butoxide (238 mg., 5 moles) and the reaction was conducted at 0° C. for 18 hours, during which time brownish red precipitate was formed. The precipitate was separated by decantation, washed with dimethoxyethane and dried to yield a crude product (369 mg.). The infra-red spectrum of this product revealed peaks at 1560 – 1580 (AcO$^-$), 1400 (AcO$^-$), 1200, 1150, 780 and 770 cm$^{-1}$ (MsO$^-$ for all the last four peaks). This suggests the presence of potassium salts of acetic and methanesulfonic acids in the product.

This crude product (369 mg.) was dissolved in water (7.3 ml.) and treated with active charcoal (369 mg.). The charcoal was then washed with water and eluated with 50% aqueous acetone. The eluate thus obtained was concentrated to yield a pale-yellow glassy residue (72 mg.).

The infra-red spectrum of this substance contained absorption bands at 3300–3500, 1610–1680 and 1050–1110 cm$^{-1}$. The thin-layer chromatographic datum (benzene methanol=1:1) of the substance corresponded to that of authentic coformycin (Rf= 0.31), but the datum (butanol:ethanol: chloroform:17% ammonia=4:5:2:4) was different from that of the latter.

This substance (96 mg.) was dissolved in water (5 ml.) and the pH value of the solution thus formed was adjusted with Dowex 1 × 2 OH$^-$) from 5.4 to 8–8.5 and allowed to stand at room temperature for 17 hours. The thin-layer chromatographic datum (butanol:ethanol:-chloroform:17% ammonia=4:5:2:4) of the substance at this point corresponded to that of authenic coformycin (Rf=0.39). The reaction solution was concentrated to yield a crude product (68 mg.). The crude product was subjected to thinlayer chromatography on three silica gel plates (20 × 20 cm), developed with a solvent (benzene: methanol=1:1), eluted with methanol to separate the portion of Rf ranging 0.25 – 0.35 and the eluate was concentrated to yield coformycin. Yield: 39 mg. (38%). Recrystallization from water gave coformycin in pure state (20 mg.).

Melting point: 178°–183° C. (coformycin naturally occurring: 181°–183.5° C.; mixture melting point: 178°–183° C.).

Specific rotation: $[\alpha]_D^{25}$ + 33.3 (c=0.6, H$_2$O) [coformycin naturally occurring: $[\alpha]_D^{25}$ + 33.8 (c=1.5, H$_2$O)].

Spectral confirmation: UV: $\lambda_{max}^{MeOH}$ ,284 nm ($\epsilon$9,200).

IR, NMR and ORD were superimposeable with those of authentic, naturally occurring coformycin.

The coformycin produced by the processes of the present invention has the structure

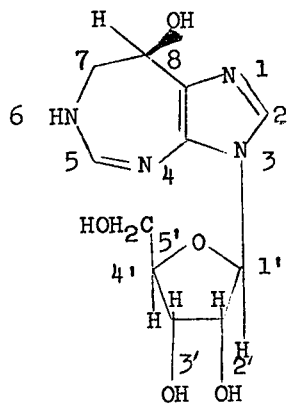

and is named 3-($\beta$-D-ribofuranosyl)-6,7,8-trihydroimidazo[4,5-d][1,3]diazepin-8(R)-ol.

Mesyl is a contraction for methylsulfonyl or methanesulfonyl and mesyl chloride is methanesulfonyl chloride having the formula CH$_3$SO$_2$Cl which is prepared from methanesulfonic acid (CH$_3$SO$_2$OH) and thionyl chloride.

Dowex 1-X2 (OH$^-$) is the basic or hydroxide form of cholestyramine resin which in its chloride form is a synthetic, strongly basic anion exchange resin containing quaternary ammonium functional groups which are attached to a styrene-divinylbenzene copolymer. Main constituent: Polystyrene trimethylbenzylammonium as Cl$^-$ anion, also contains divinylbenzene (about 2%) and water

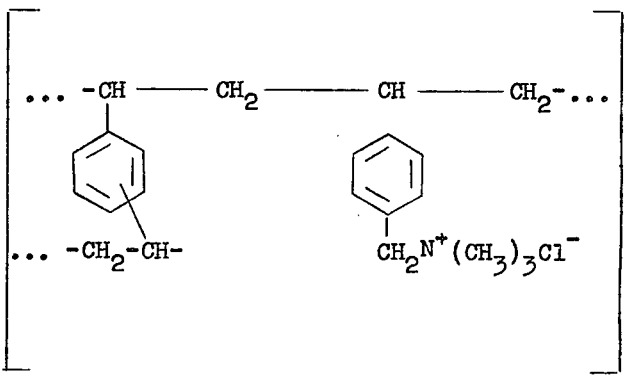

typified structure of main polymeric groups (about 43%). Cross linkage %: 1–10. Particle size: 50–100 mesh. Percent volume increase, new to exhausted (Cl$^-$ to OH$^-$) = 20%. Stable at temperatures up to 150°. Capacity: 3.5 meq/g dry, 1.33 meq/ml wet.

We claim:
1. A process for the preparation of coformycin of the formula (I):

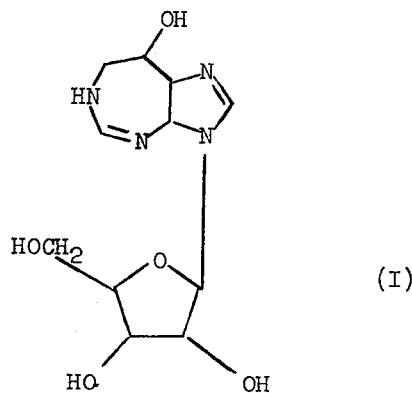

which comprises treating 9-(2,3,4-tri-O-acetyl-$\beta$-D-ribo-furanosyl)-6-mesyloxymethyl-1,6-dihydropurine of the formula (II)

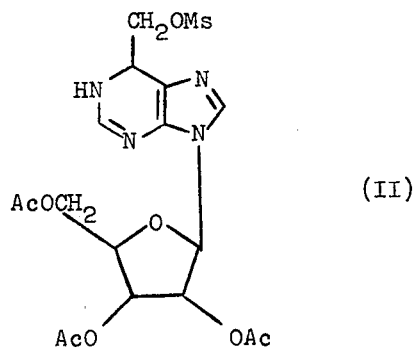

in which Ac represents acetyl and Ms represents mesyl with potassium tert.-butoxide as a base under cooling in dimethoxyethane and hydrolyzing the resulting intermediate product by dissolving it in water at a pH in the range of 5.4 to 8.5 and allowing the solution to stand until hydrolysis is complete.

2. A compound having the formula:

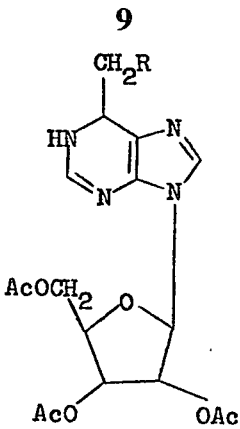
in which Ac represents acetyl and R represents hydroxyl or O-mesyl.
3. 9-(2,3,4-tri-O-Acetyl-β-D-ribofuranosyl)-6-mesyloxymethyl-1,6-dihydropurine.
4. 9-(2,3,5-tri-O-Acetyl-β-D-ribofuranosyl)-6-hydroxymethyl-1,6dihydropurine.
* * * * *

UNITED STATES PATENT OFFICE
CERTIFICATE OF CORRECTION

Patent No. 3,959,257    Dated May 25, 1976

Inventor(s) Hamao Umezawa et al

It is certified that error appears in the above-identified patent and that said Letters Patent are hereby corrected as shown below:

In column 8, line 28, change "9-(2,3,4-tri-O-acetyl-β-D-" to read --9-(2,3,5-tri-O-acetyl-β-D- --.

In column 10, line 3, change "9-(2,3,4-tri-O-Acetyl-β-D-ribofuranosyl)-6-" to read --9-(2,3,5-tri-O-Acetyl-β-D-ribofuranosyl)-6- --.

In column 10, line 6, change "hydroxymethyl-1,6dihydropurine' to read --hydroxymethyl-1,6-dihydropurine--.

Signed and Sealed this

Second Day of November 1976

[SEAL]

*Attest:*

RUTH C. MASON
*Attesting Officer*

C. MARSHALL DANN
*Commissioner of Patents and Trademarks*